(12) United States Patent
Braach-Maksvytis et al.

(10) Patent No.: US 6,562,631 B2
(45) Date of Patent: May 13, 2003

(54) DETECTION DEVICE AND METHOD

(75) Inventors: Vijoleta Lucija Bronislava Braach-Maksvytis, Dulwich Hill (AU); Bruce Andrew Cornell, Neutral Bay (AU); Lionel George King, North Ryde (AU); Burkhard Raguse, St. Ives (AU)

(73) Assignees: Australian Membrane and Biotechnology Research Institute, Homebush (AU); The University of Sydney, Sydney (AU)

( * ) Notice: Subject to any disclaimer, the term of this patent is extended or adjusted under 35 U.S.C. 154(b) by 0 days.

(21) Appl. No.: 08/856,552

(22) Filed: May 15, 1997

(65) Prior Publication Data

US 2002/0164826 A1 Nov. 7, 2002

(30) Foreign Application Priority Data

Nov. 16, 1994 (AU) .............................................. PM9500

(51) Int. Cl.[7] ...................... G01N 33/561; G01N 15/06; G01N 33/53; G01N 25/18

(52) U.S. Cl. ........................ 436/518; 422/50; 422/68.1; 422/82.01; 422/82.02; 435/4; 435/7.1; 435/7.2; 435/287.1; 435/287.2; 436/149; 436/501; 436/512; 436/514; 436/532; 436/806

(58) Field of Search ...................... 422/50, 68.1, 82.01, 422/82.02; 435/4, 7.1, 7.2, 287.1, 287.2; 436/149, 501, 512, 514, 518, 532, 806

(56) References Cited

U.S. PATENT DOCUMENTS

| 4,713,347 A | 12/1987 | Mitchell et al. | ............ 436/501 |
| 5,234,566 A | 8/1993 | Osman et al. | ............ 204/403 |
| 5,328,847 A | 7/1994 | Case et al. | ............ 435/291 |

FOREIGN PATENT DOCUMENTS

| EP | 0342382 | 11/1989 | .......... G01N/33/543 |
| WO | 9008783 | 8/1990 | .......... C07K/17/08 |
| WO | 9321528 | 10/1993 | .......... G01N/33/543 |
| WO | 9407593 | 4/1994 | .......... B01D/67/00 |
| WO | 9412875 | 6/1994 | .......... G01N/33/48 |
| WO | 9615454 | 5/1996 | .......... G01N/33/558 |

OTHER PUBLICATIONS

Supplementary European Search Report; Appln. No.–EP 95937724 Sept. 16, 1999.

*Primary Examiner*—Rodney P. Swartz
(74) *Attorney, Agent, or Firm*—Gottlieb, Rackman & Reisman P.C.

(57) ABSTRACT

The present invention provides an analyte detection device. The device comprises first and second zones, means to allow addition of a probe to the first zone, means to allow addition of a sample suspected to contain an analyte and means to allow passage of the probe from the first zone to the second zone. The first zone contains ligands reactive with the analyte and the second zone includes a membrane the impedance of which is dependent on the presence or absence of the probe and means to measure the impedance of the membrane. It is preferred that the probe includes an ionophore, preferably gramicidin. The present invention also relates to methods of detecting the presence of an analyte.

16 Claims, 14 Drawing Sheets

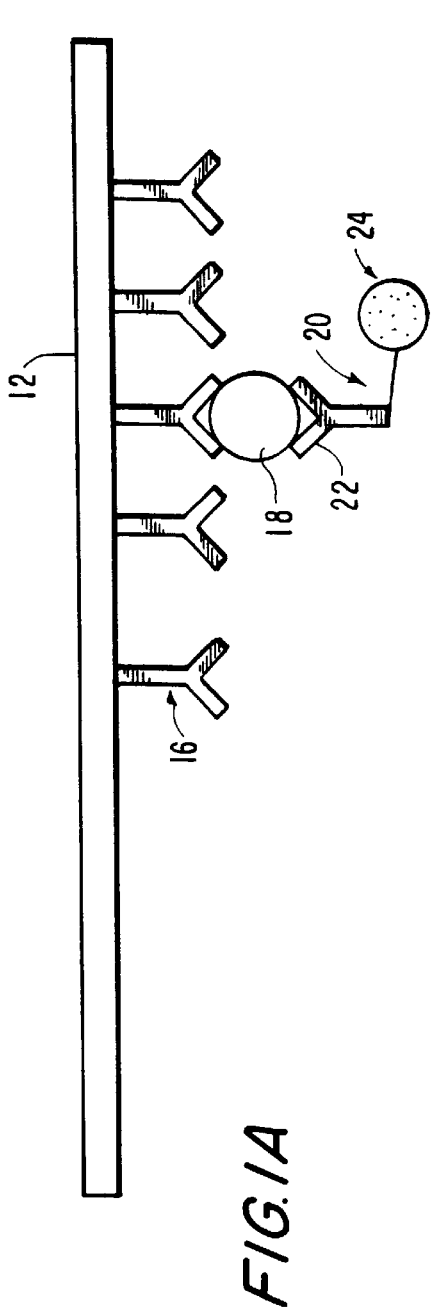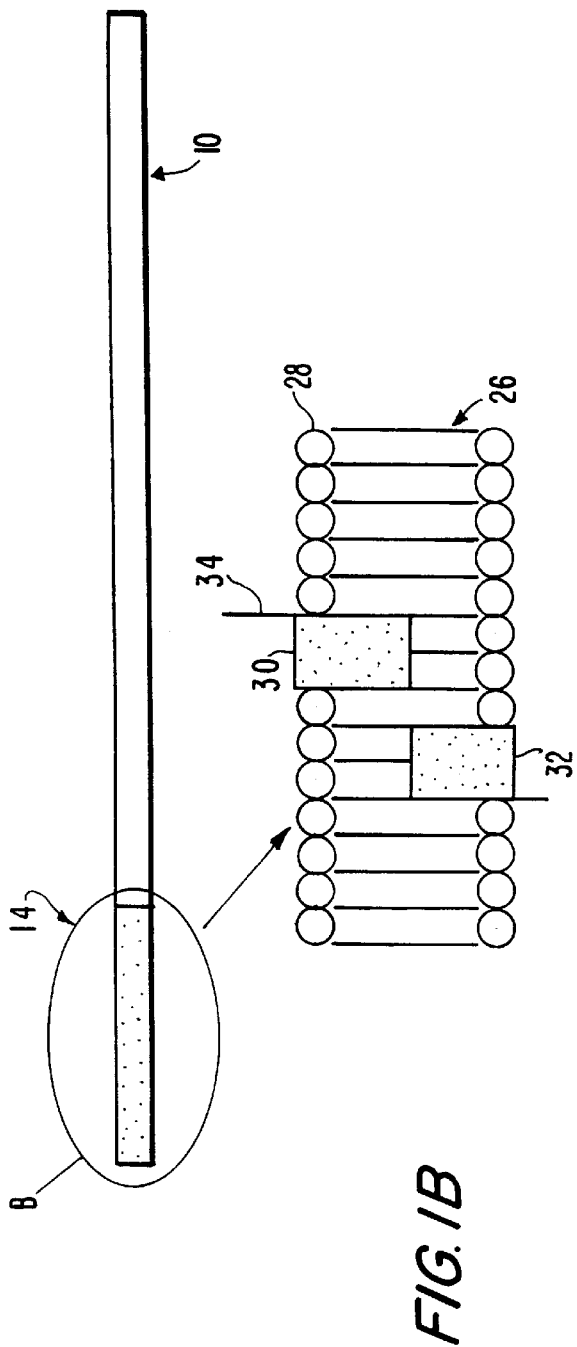
FIG.1A
FIG.1B

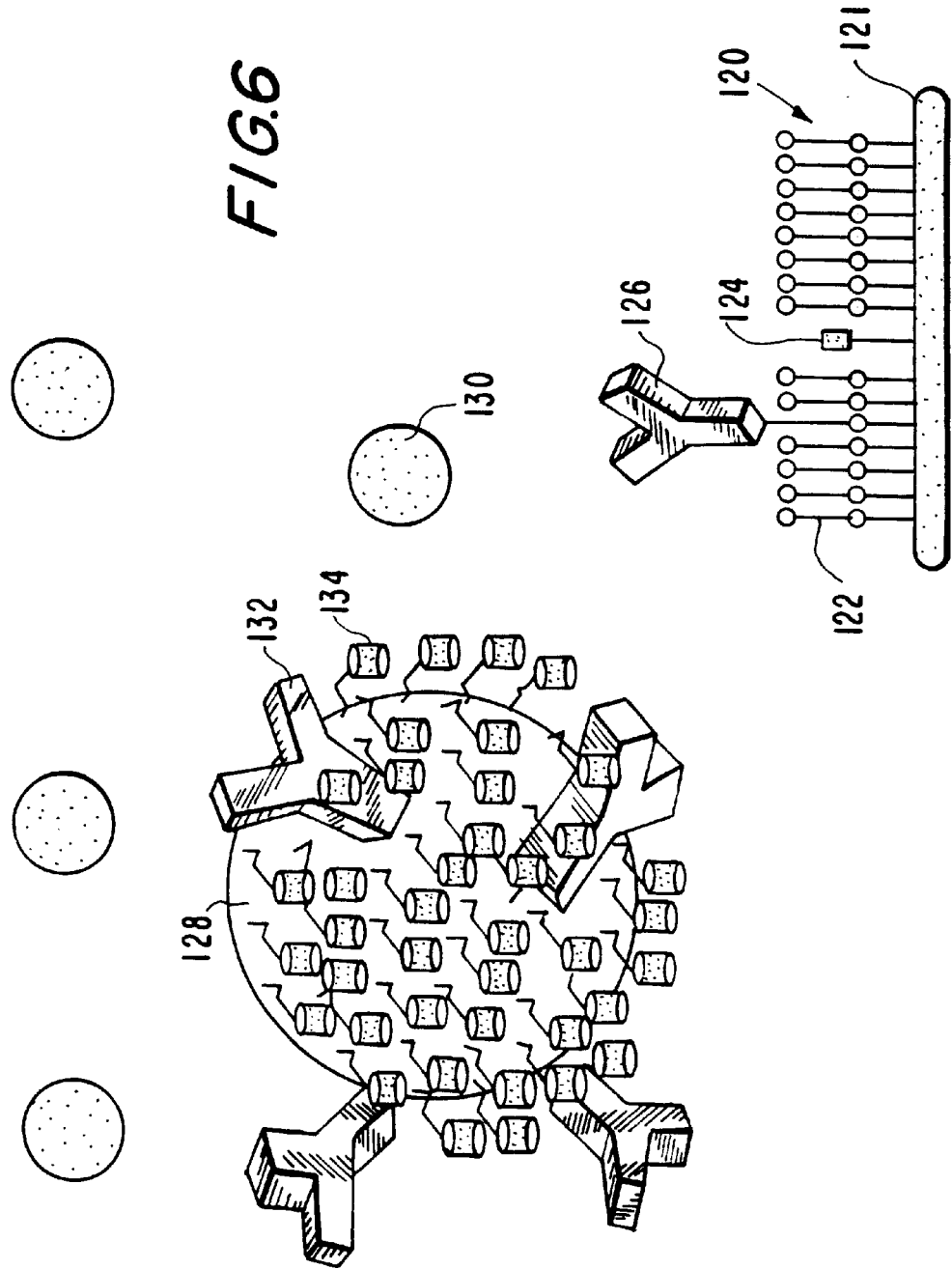

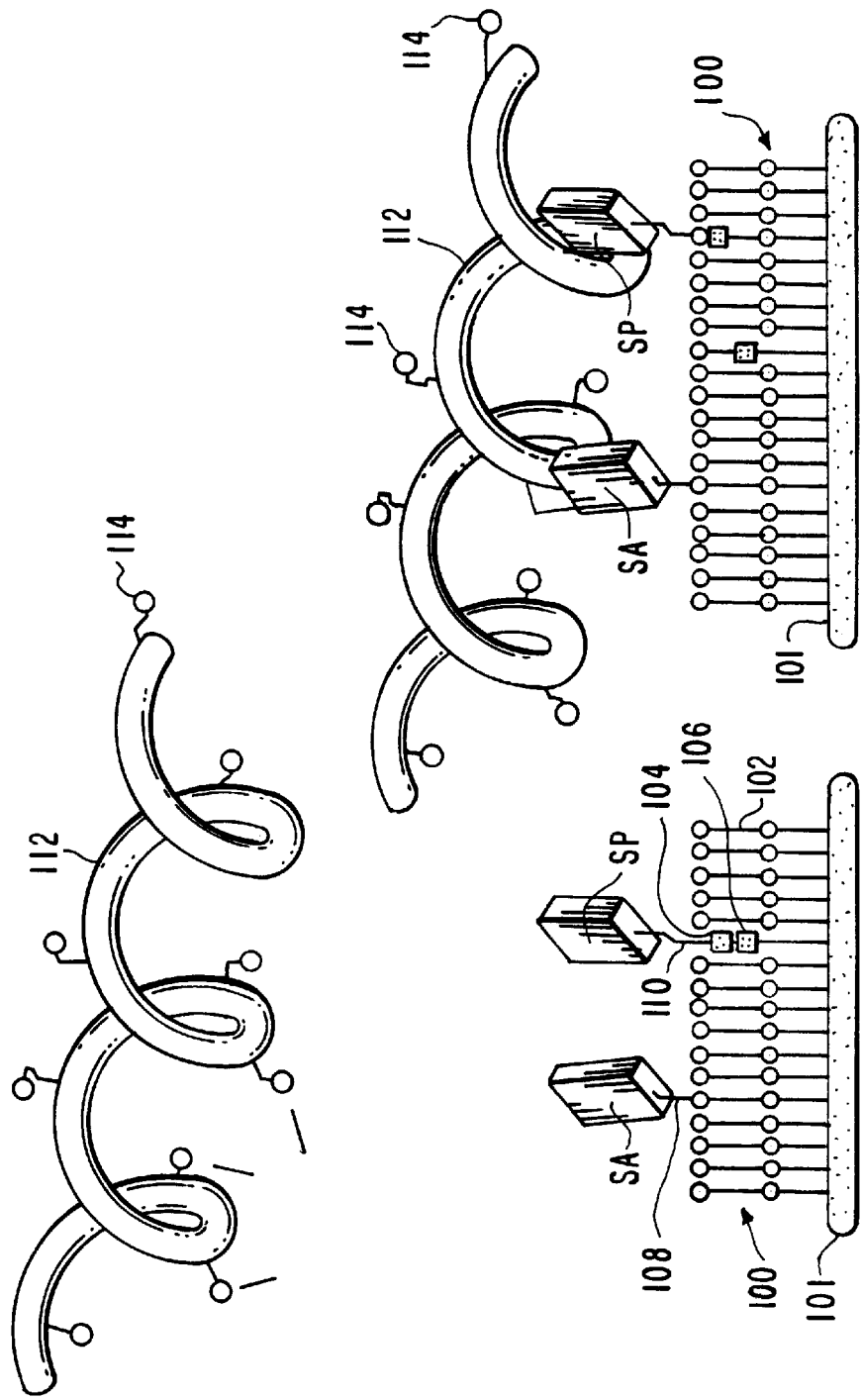

Linker Lipid A

Linker Gramicidin B

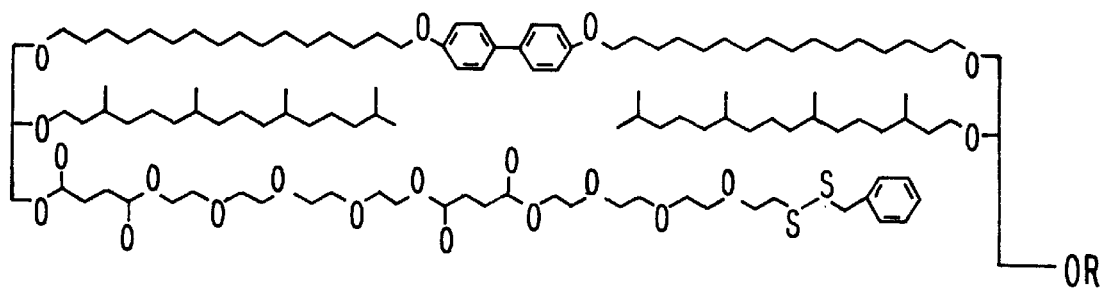
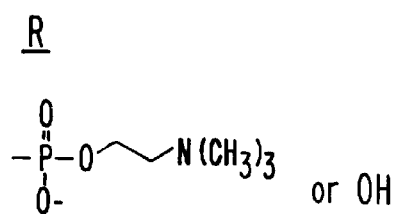 or OH
Membrane Spanning Lipid D
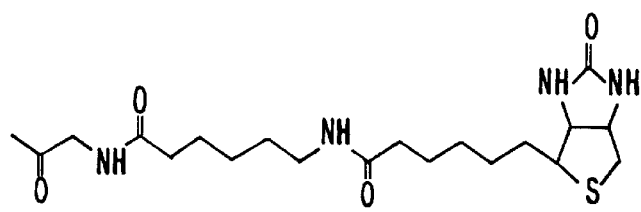
Membrane Spanning Lipid C
FIG. 10

Biotinylated Gramicidin E

DETECTION DEVICE AND METHOD

The present invention relates to a device for the detection of an analyte in a sample and to a method of detecting the presence of an analyte in a sample.

Current technologies used in the diagnostic industry require large expensive equipment for the detection of analytes. For example, immunoassays require gamma-detectors, spectrophotometers, lasers, etc. and DNA detection after PCR processes requires electrophoresis and absorption methods, all of which depend on the specific probe used for signal amplification.

A number of devices have been described in the literature which have been designed for simple single-step assays and make use of area separation to carry out the different reactions and washing steps required. For example, antibody-based tests such as the pregnancy testing device "Clearblue One-Step" by Unipath employ a wick to absorb urine which then travels the length of a pen-like device. The hormone hCG is captured by the first layer which contains mobile blue latex particles to which mAb has been coupled. The urine flow carries the latex, and bound hCG, to a second area containing immobilized mAb recognizing a second epitope site on the hormone. Any hCG bound to the latex will be prevented from continuing past the second area as evidence by a discrete blue line. In the absence of hCG, the latex moves through to a third area and captured by immobilized anti-Fc antibody. Other disposable devices use liquid-operated switch (illustrated in FIG. 12.7 Chapter 12 by A. P. H. Farnsworth, in "Molecular and Antibody Probes in Diagnosis" edited by M. R. Walker and R. Rapley, John Wiley and sons, 1993) to carry out sequential steps in the ELISA-type processes. In DNA-based technologies, a product for performing the multiple steps required in PCR technology has been released which by compartmentalizing the different steps in a single disposable device offers simplicity and reduction of cross-contamination of the PCR products.

In International Patent Application Nos. PCT/AU88/00273, PCT/AU89/00352, PCT/AU90/00025, PCT/AU92/00132, PCT/AU93/00590, PCT/AU93/00620 and PCT/AU94/00202 there is disclosure of biosensors which can be used to detect analytes. The disclosure of these documents is included herein by cross-reference.

It is believed that by adapting these biosensors and existing diagnostic techniques improved detection devices and methods of detection can be achieved.

Accordingly in a first aspect the present invention consists in an analyte detection device comprising first and second zones, means to allow addition of a probe to the first zone, means to allow addition of a sample suspected to contain an analyte to the first zone, and means to allow passage of the probe from the first zone to the second zone; the first zone containing ligands reactive with the analyte and the second zone including a membrane the impedance of which is dependent on the presence or absence of the probe and means to measure the impedance of the membrane.

The means to allow addition of the probe and sample to the first zone may be the same or different.

In a preferred embodiment of the present invention the probe includes an ionophore, preferably gramicidin.

In a further preferred embodiment of the present invention the membrane comprises a first and second layer of closely packed arrays of amphiphilic molecules and a plurality of ionophores comprising a first and second half membrane spanning monomers, the first half membrane spanning monomers being provided in the first layer and the second half membrane spanning monomers being provided in the second layer, the second half membrane spanning monomers being capable of lateral diffusion within the second layer independent of the first half membrane spanning monomers, the first half membrane spanning monomers being prevented from lateral diffusion in the first layer, and a second ligand provided on at least the second half membrane spanning monomers, said second ligand being reactive with the probe or a portion thereof, the binding of the probe to the second ligand causing a change in the relationship between the first half membrane spanning monomers and the second half membrane spanning monomers such that the flow of ions across the membrane via the ionophores is allowed or prevented, and measuring the impedance of the membrane.

In yet another preferred embodiment the ligands in the first zone are antibodies or binding fragments thereof.

In a second aspect the present invention consists in a method of detecting the presence of an analyte in a samnple, the method comprising contacting the sample with a carrier including a plurality of first ligands reactive with the analyte to allow binding of the analyte to the carrier ligands, contacting the carrier with a membrane comprising a first and second layer of a closely packed array of amphiphilic molecules and a plurality of ionophores comprising a first and second half membrane spanning monomers, the first half membrane spanning monomers being provided in the first layer and the second half membrane spanning monomers being provided in the second layer, the second half membrane spanning monomers being capable of lateral diffusion within the second layer independent of the first half membrane spanning monomers, the first half membrane spanning monomers being prevented from lateral diffusion in the first layer, and a second ligand provided on at least the second half membrane spanning monomers, said second ligand being reactive with the analyte or a portion thereof, the binding of the analyte to the second ligand causing a change in the relationship between the first half membrane spanning monomers and the second half membrane spanning monomers such that the flow of ions across the membrane via the ionophores is allowed or prevented, and measuring the impedance of the membrane.

The first half membrane spanning monomer in the first layer may be prevented from diffusing laterally using any of a number of known techniques, however, it is presently preferred that the monomer and the amphiphilic molecules each include or are decorated with at least one moiety cross-linked with at least one corresponding moiety on another of these molecules. Under appropriate stimulus, such as W radiation or ionizing radiation, the cross-linkable moieties can be caused to polymerize thereby resulting in the membrane being cross-linked in one layer.

The first half membrane spanning monomers may also be prevented from diffusing laterally by selecting lipids for the first layer of the membrane which are crystalline at room temperature. This eliminates lateral diffusion in the first layer.

In a further preferred embodiment of the present invention the first half membrane spanning monomers in the first layer are prevented from diffusing laterally by fixing the first layer and the monomers therein to a solid support. This may be achieved by providing groups on the amphiphilic molecules in the first layer and on the monomers therein which are reactive with the solid support or with corresponding groups provided thereon.

In another prefered form of the invention a proportion of the amphiphlic molecules are membrane spanning amphiphiles, the membrane spanning amphiphiles being archeobacterial lipids or tail to tail chemically linked bilayer amphiphiles. It is also preferred that the half membrane spanning monomers are gramicidin monomers.

In yet another preferred embodiment the membrane includes a plurality of third ligands attached to amphiphiles in the membrane, preferably membrane spanning amphiphiles. These third ligands are preferably prevented from diffusing laterally within the membrane. In the device of the first aspect of the present invention these third ligands will be reactive with probe or a portion thereof, whilst in the method of the second aspect of the present invention they will be reactive with the analyte.

The ligands may be the same or different and are preferably selected from the group consisting of polyclonal or monoclonal antibodies, antibody fragments including at least one Fab fragment, antigens, lectins, haptens, chelating agents and dyes.

The ligands are preferably attached to the ionophores and/or membranes via linkers. Suitable linkers are set out in PCT/AU90/00025, PCT/AU92/00132 and PCT/AU93/00509.

As will be recognized by those skilled in this field it is preferable that the membrane is attached to an electrode such that a reservoir exists between the electrode and the membrane. Molecules and methods by which this may be readily achieved are set out in PCT/AU92/00132 and PCT/AU93/00509. As stated above the disclosures of these documents are incorporated by cross reference.

In a third aspect the present invention consists in an analyte detection device comprising:
 membrane including ligands reactive with an analyte;
 means to measure the impedance of the membrane; and
 means to move an analyte bound to the ligands away from the membrane without disrupting the binding of the ligands to the analyte;
wherein the movement of the analyte away from the membrane causes a change in the impedance of the membrane.

In a preferred embodiment of this aspect of the present invention the analyte is bound to a carrier via a plurality of second ligands. Preferably the carrier is a bead, or a charged or magnetic particle.

In a preferred embodiment the means to move the analyte comprises an electric field, magnetic field or liquid flow.

In another preferred embodiment the membrane ligands are attached to amphiphiles of the membrane, movement of the analyte causing extraction of the ligands and attached amphiphiles from the membrane.

In yet another preferred embodiment the membrane ligands are attached to ionophores within the membrane, movement of the analyte causing extraction of the ligands and attached ionophores from the membrane. The ionophores are preferably gramicidin.

In a fourth aspect the present invention consists in a method of determining the presence or absence of an analyte in a sample, the method comprising adding the sample to the device of the first or third aspect of the present invention and measuring a changing conductivity or capacitance of the membrane.

In a preferred embodiment of the present invention the membrane is as described in International Patent Application Nos. PCT/AU88/00273, PCT/AU89/00352, PCT/AU90/00025, PCT/AU92/00132, PCT/AU93/00590, PCT/AU93/00620 or PCT/AU94/00202.

In order that the nature of the present invention may be more clearly understood preferred forms thereof will now be described with reference to the following examples and figures in which:

FIG. 1A shows a schematic representation of an embodiment of the analyte detection device of the present invention.

FIG. 1B is an expanded view of Region B of FIG. 1a.

FIG. 6 is a schematic representation of another embodiment of the method and device of the present invention.

FIGS. 7A and 7B are schematic representations of an embodiment of the present invention used in the detection of DNA.

FIG. 10 shows the structure of membrane spanning lipid D.

Figure 2:
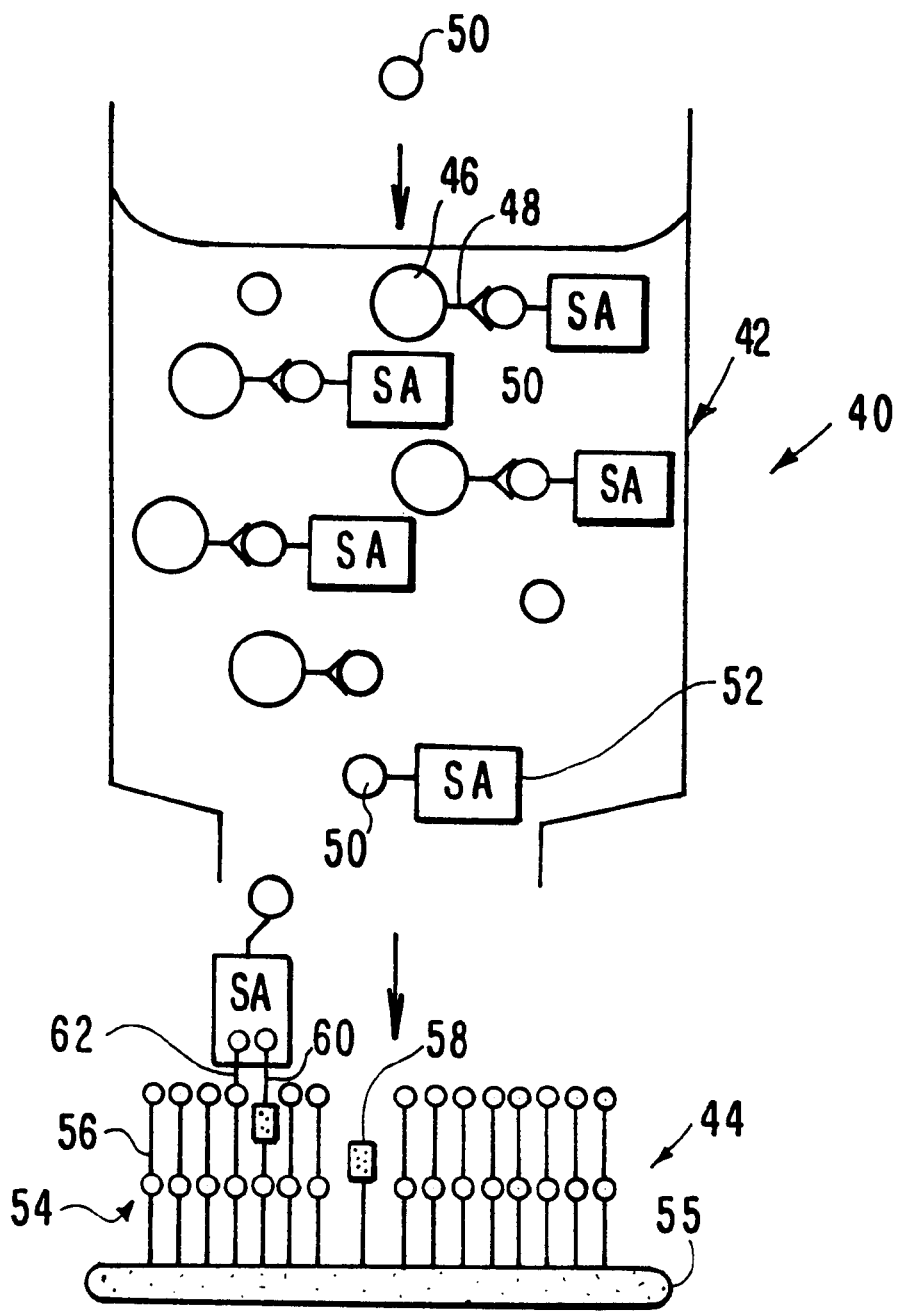
FIG. 2 is a schematic representation of another embodiment of the analyte detection device of the present invention.

As shown in FIG. 1A the device 10 consists of two zones 12 and 14. Zone 12 is provided with ligands 16 reactive with analyte 18. The probe 20 consists of a ligand 22 reactive with analyte 18 and a marker 24.

Zone 14 includes a sensing membrane 26. The membrane 26 comprises amphiphilic molecules 28 and ionophores 30 and 32. Ionophore 30 includes ligand 34 which is reactive with marker 24.

In operation a sample suspected of containing analyte 18 is added to zone 12. Probe 20 is also added to zone 12. In the situation shown in FIG. 1A the analyte 18 binds to ligands 16 and is thereby immobilized. Ligand 22 of probe 20 then also binds to analyte 18 and thereby immobilizes the probe. The probe 20 is therefore unable to travel to zone 14 including sensing membrane 16. If the analyte is not present the probe 20 is then free to travel to zone 14 and sensing membrane 26. Upon reaching sensing membrane 26 the marker 24 binds to ligand 34 causing a change in impedance of the membrane.

FIG. 2 shows another embodiment of the analyte detecting device. The analyte detecting device 40 comprises zones 42 and 44. Zone 42 includes carrier 46 to which are attached ligands 48 reactive with analyte 50. As shown in FIG. 2 zone 42 also includes probe 52 which comprises analyte 50 and marker SA (streptavidin). Zone 44 includes a sensing membrane 54 and electrode 55. The sensing membrane 54 consists of amphiphiles 56 ionophores 58 and ligands 60 and 62 which are attached to ionophores 58 and amphiphiles 56 respectively.

In operation analyte 50 is added to zone 42. The analyte 50 competes with the analyte 50 component of probe 52 for binding to ligand 48. As shown in FIG. 2 this results in the release of probe 52 which includes streptavidin. The probe 52 then passes to zone 44 and sensing membrane 54. The streptavidin then binds with ligands 60 and 62 causing a change in impedance of the sensing membrane 54. Clearly, if the sample added did not include analyte 50 probe 52 would not be released and the streptavidin would not reach the sensing membrane 54.

Figure 3:
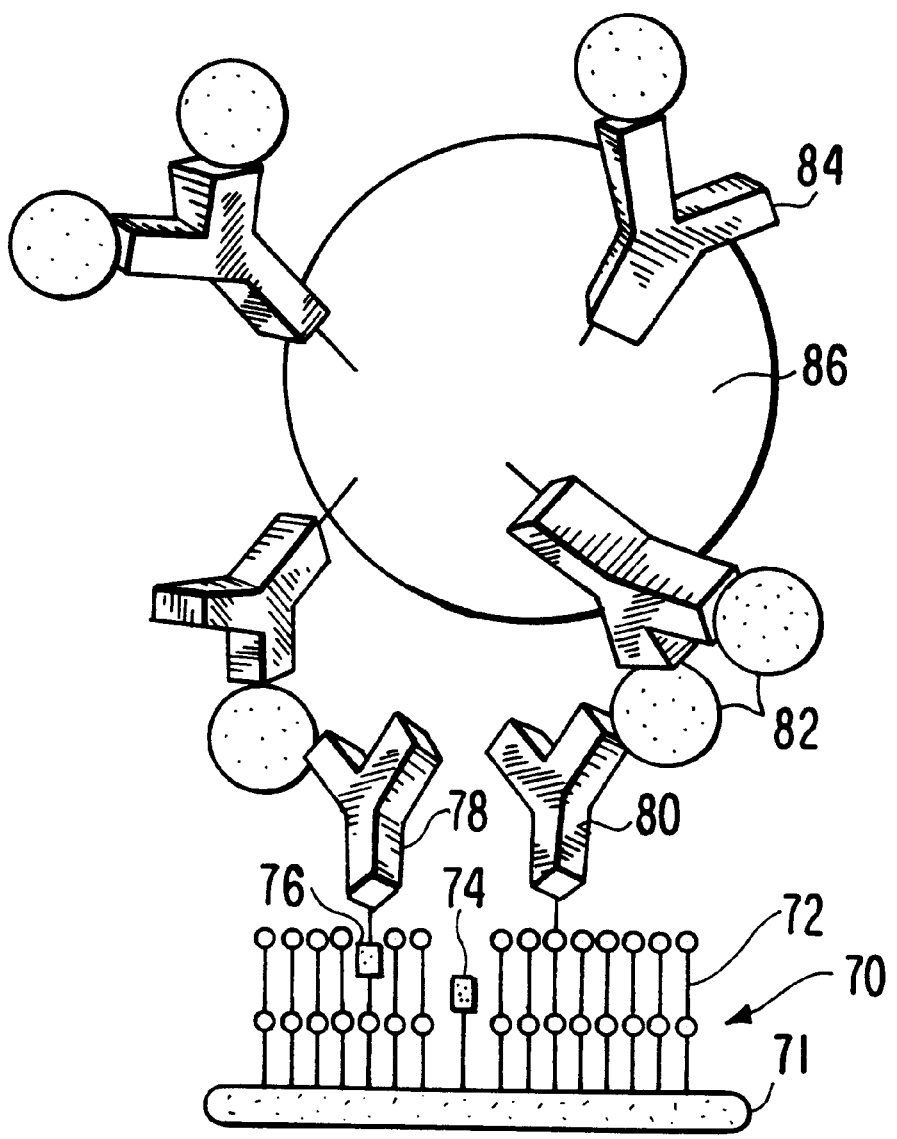
FIG. 3 is a schematic representation of an embodiment of the method of the present invention.

FIG. 3 shows an embodiment of the method of the present invention. The method involves the use of a sensing membrane 70 comprising amphiphiles 72 and ionophores 74 and 76 and electrode 71. Ligands 78 and 80 reactive with analyte 82 are attached to ionophores 76 and amphiphiles 72 respectively. A carrier bead 86 provided with a plurality of ligands 84 reactive with analyte 82 is also provided. The binding at the analyte 82 which is attached to the carrier bead 86 via ligands 84 to ligands 78 and 80 causes a change in impedance of the membrane 70.

Figure 4B:
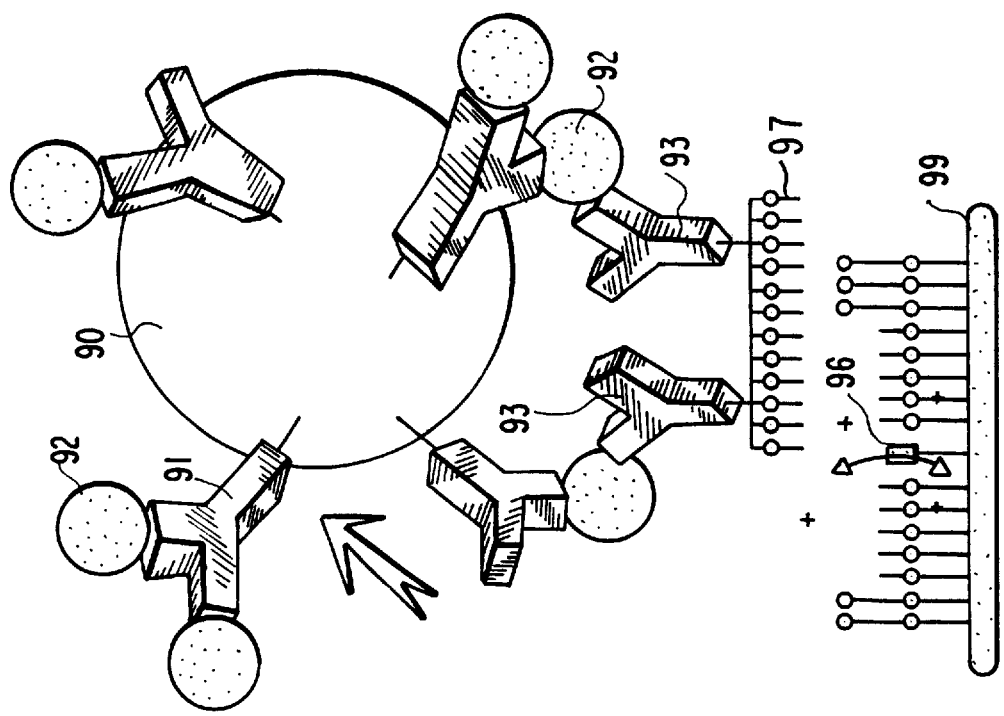
FIGS. 4A and 4B are schematic representations of an embodiment of the detection device of the present invention.
Figure 4A:
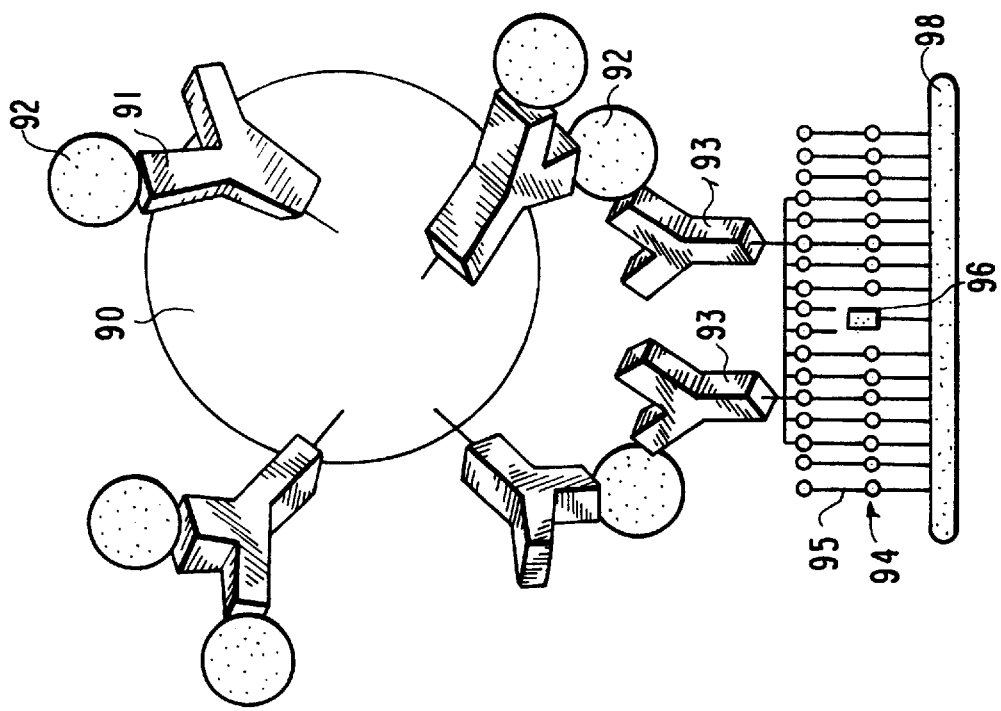

FIG. 4 shows schematically the operation of an embodiment of the device of the present invention. As shown in FIG. 4A an analyte 92 is bound to a carrier 99 via ligands 91. A sensing membrane 94 comprising amphiphiles 95 and ionophores 96 and electrode 99 is also provided. The analyte 92 is bound to the sensing membrane 94 via ligands 93. In FIG. 4b the carrier 99, and thereby analyte 92, has been moved away from the sensing membrane 94. This may be achieved by the application of force due to an electric field, magnetic field or liquid flow. The movement of the particle 90 causes the extraction of a segment 97 of the sensing membrane 95. This results in an increased ability for ions to pass through the membrane thereby resulting in a change in impedance of the sensing membrane 94.

Figure 5B:
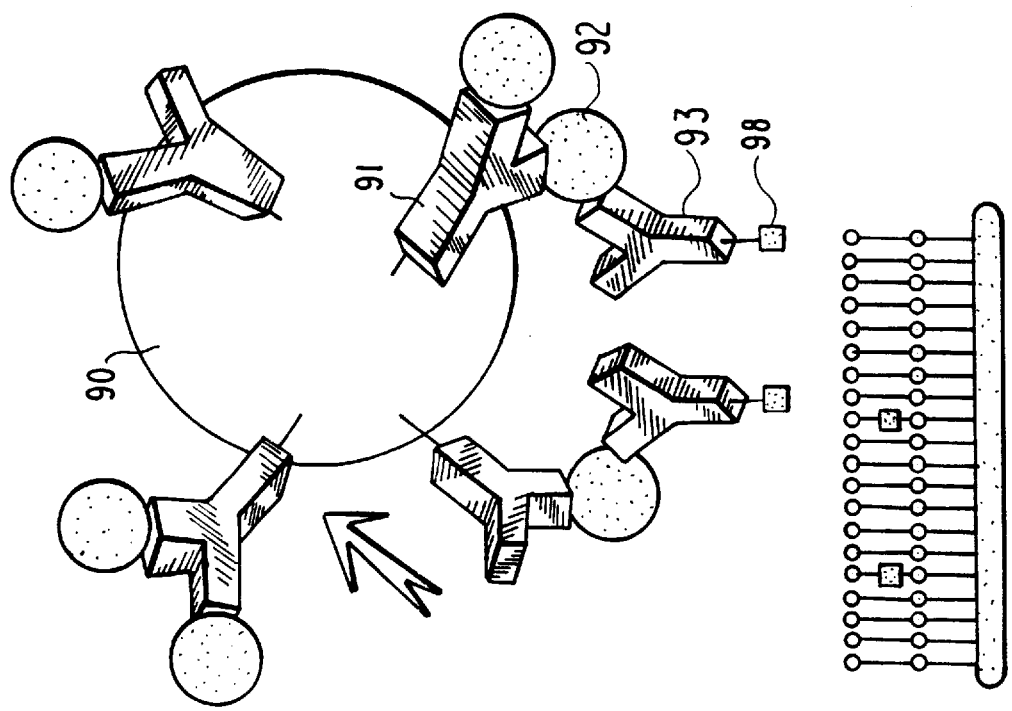
FIGS. 5A and 5B are schematic representations of another embodiment of the detection device of the present invention.
Figure 5A:
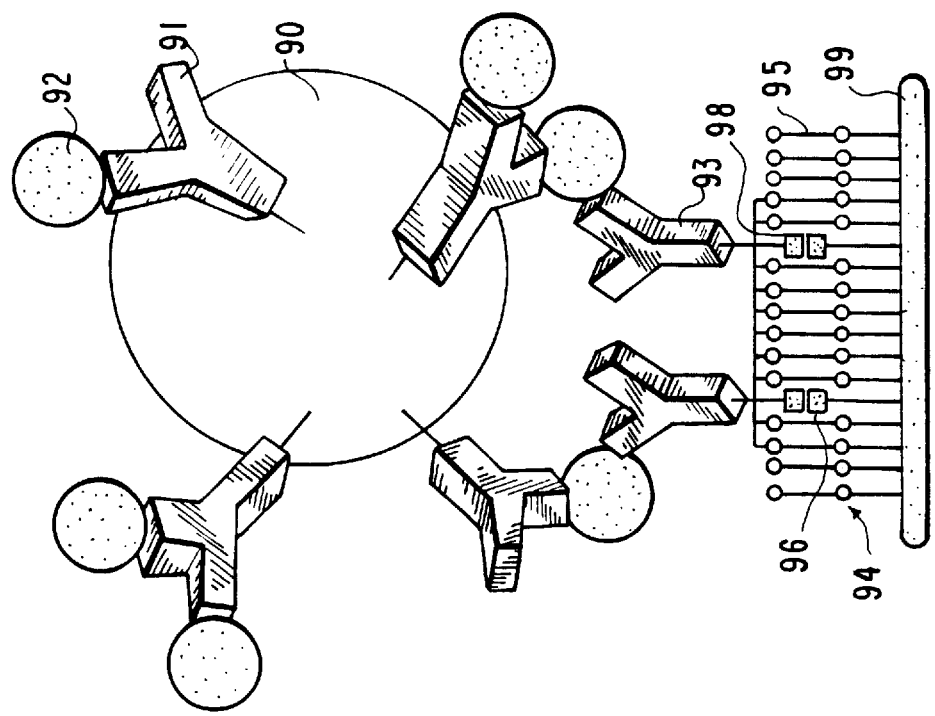

FIG. 5 shows an alternate embodiment to that shown in FIG. 4. In this arrangement movement of the carrier 90 away from the membrane results in extraction of ionophores 98 from the membrane. The removal of these ionophores will result in a decrease in the ability of ion to pass through the membrane and therefore result in a change in impedance of the membrane.

FIG. 6 shows an alternate embodiment to that shown in FIG. 3. In this embodiment a sensing membrane 120 comprising amphiphiles 122, ionophores 124 and ligands 126 reactive with analyte 130 is provided. An electrode 121 is also provided. A carrier bead 128 provided with a plurality of ligands 132 reactive with analyte 130 and a plurality of ionophores 134 is also provided. The binding at the anlyte 130 to ligands 126 and 132 results in the insertion of ionphores 134 into the membrane 120 thereby causing a change in impedance of the membrane 120.

FIG. 7 shows a schematic representation of the detection of DNA. FIG. 7A shows the sensing membrane 100 composed of amphiphiles 102 and ionophores 104 and 106 and electrode 101. Streptavidin (SA) is attached to the amphiphiles 102 and ionophores 106 via linkers 108 and 110 respectively. As shown in FIG. 7B biotin 114 on DNA 112 binds to the streptavidin which causes a gating of the membrane 100 resulting in a change of impedance of the membrane 100.

As will be appreciated, the representations in FIG. 7 are an embodiment of the second zone of the device of the present invention in which the biotin labelled DNA functions as the probe.

As will be recognized by those skilled in the art the present invention has general applicability, for example:

1. Generic homogenous capillary/column sensor—use with Ab-Ag-Ab sandwich
   a) DIRECT ASSAY: Sample added to assay device. Capillary action drives the sample into contact with Ab labelled with probe. Further travel enables the Ag-Ab complex to bind to a second Ab immobilised on capillary wall which captures Ag-Ab complex. In the absence of analyte, the second Ab labelled with probe diffuses to the biosensor membrane where it elicits a change of impedance (FIG. 1).

The detection probe may be anything that upon incorporation into or accrual onto the bilayer membrane elicits an impedance change (whether increase or decrease in signal). Examples of detection probes include streptavidin, gramicidin, gramicidin/detergent (e.g. SDS, octylglucoside) aggregate, gramicidin/vesicle, gramicidin/polystyrene beads, etc. Where the probe is streptavidin, the membrane would contain biotinylated gramicidin; if the probe contains gramicidin, the membrane would initially contain no gramicidin. Where the probe is an antibody the membrane would contain a gramicidin-hapten or gramicidin-antigen conjugate.

b) COMPETITIVE ASSAY: as described for a) except that the sandwich is preformed between Ab-Ag or Ag analogue-Ab. As the sample is introduced, the analyte in the sample competes off the labelled second Ab, eliciting an impedance change at the biosensor membrane.

2. Streptavidin Sensor

Bead column comprised of e.g. polystyrene beads coupled to Ab. A covalently linked conjugate of analyte or analyte analogue and streptavidin are bound to the Ab. When sample is introduced containing the analyte, the analyte competes off the SA/analyte conjugate, releasing SA. SA binds to biotinylated gramicidin in the biosensor membrane changing the impedance signal (FIG. 2). Can also be used in capillary mode as described in 1, above. It will also be readily appreciated by persons skilled in the art that such an arrangement may be used with labels (probes) other than SA. For example SA could be replaced with a hapten and the gramicidin in the membrane would, as opposed to being biotinylated, would have bound thereto a receptor for the hapten.

3. Methods of detecting Ab-Ag-Ab sandwich involving Ab-bead conjugates
   a) LATERAL SEGREGATION; Ab-coated beads capture sample analyte. Sandwich complex is completed with Ab linked to gramicidin and membrane spanning lipid, causing lateral segregation of channels which results in impedance change (see FIG. 3).
   b) LARGE PARTICLES INDUCING CURRENT LEAKS: Ab-coated large beads capture sample analyte. Sandwich complex is completed with Abs linked to membrane components which are themselves cross-linked into domains (membrane may contain no channels). Application of liquid flow at high velocity, removes a section of the biosensor membrane via the domains resulting in electrical leakage. See FIG. 4.
   c) LARGE PARTICLES REMOVING ION CHANNELS: Ab-coated large beads capture sample analyte. Sandwich complex is completed with Ab linked to gramicidin in the biosensor membrane. Application of liquid flow at high velocity, removes the gramicidin from the biosensor membrane resulting in turning "off" the electrical signal. See FIG. 5.
   d) MAGNETIC PARTICLES INDUCING CURRENT LEAKS: Ab-coated charged magnetic beads capture sample analyte. Sandwich complex is completed with Abs linked to membrane components which are themselves cross-linked into domains (contains no channels). Application of electric field, or magnetic field, removes a section of the biosensor membrane via the domains resulting in electrical leakage. See FIG. 4.
   e) MAGNETIC PARTICLES REMOVING ION CHANNELS: Ab-coated charged magnetic beads capture sample analyte. Sandwich complex is completed with Ab linked to gramicidin in the biosensor membrane. Application of electric field, or magnetic field, removes the gramicidin from the biosensor membrane resulting in turning "off" the electical signal. See FIG. 5.

f) BEAD INSERTING ION CHANNELS INTO MEMBRANE: Ab-coated beads coated with gramicidin channels capture sample analyte. Sandwich complex is completed with Ab linked to components in the membrane (contains no ion channels). The proximity of the beads to the surface allows for the insertion of gramicidin channels on the beads into the membrane, resulting in conduction across the membrane. See FIG. 6.

4. Method of detecting PCR products

Sample DNA is amplified using known PCR technology to generate biotinylated-DNA. Biotinylated-DNA is passaged to biosensor membrane containing SA linked to either gramicidin only or gramicidin and membrane spanning lipids, to directly or using lateral segregation, respectively, turn "off" the membrane. See FIG. 7.

EXAMPLE 1

Preparation of Sensing Membrane

Figure 8:
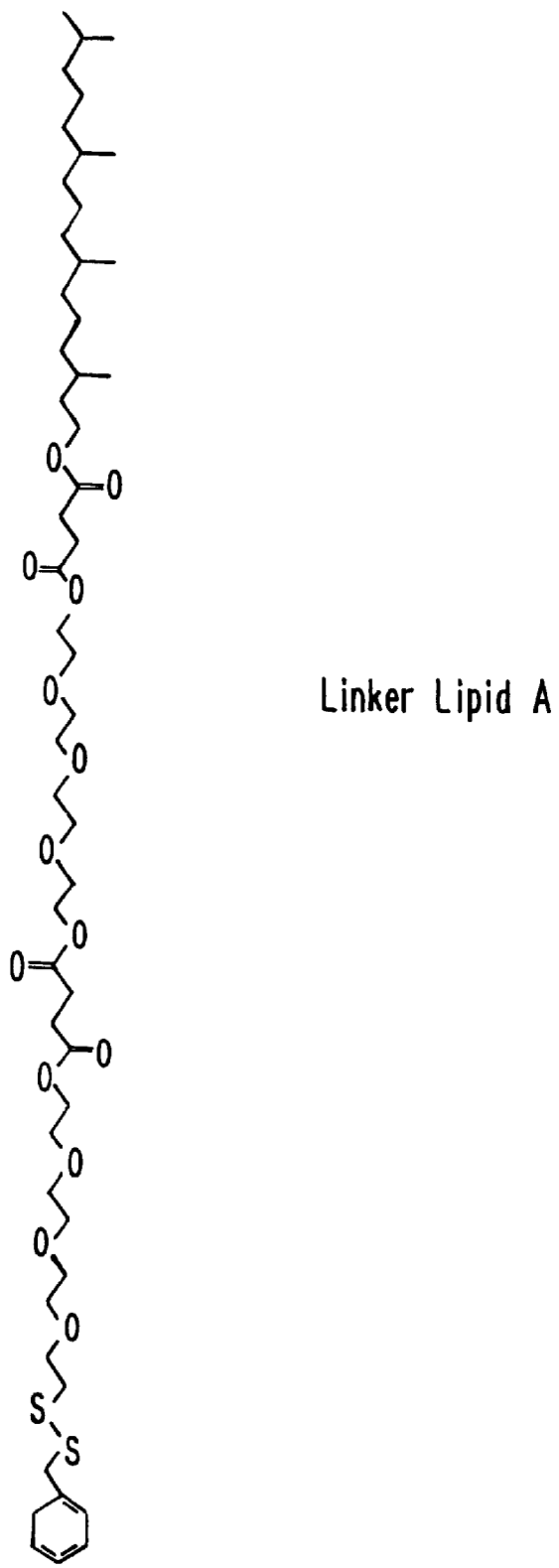
FIG. 8 shows the structure of linker lipid A.
Figure 9:
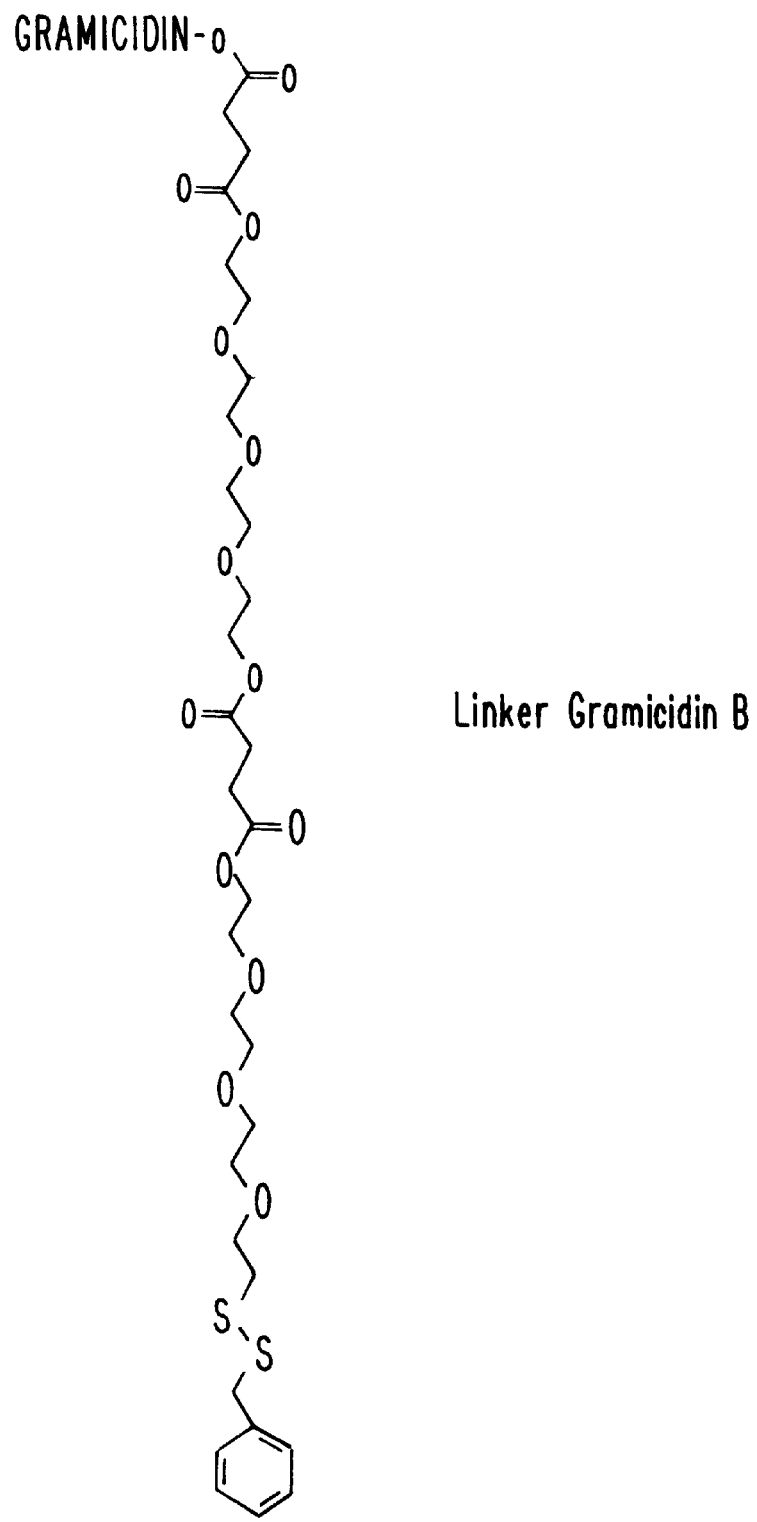
FIG. 9 shows the structure of linker gramicidin B.
Figure 11:
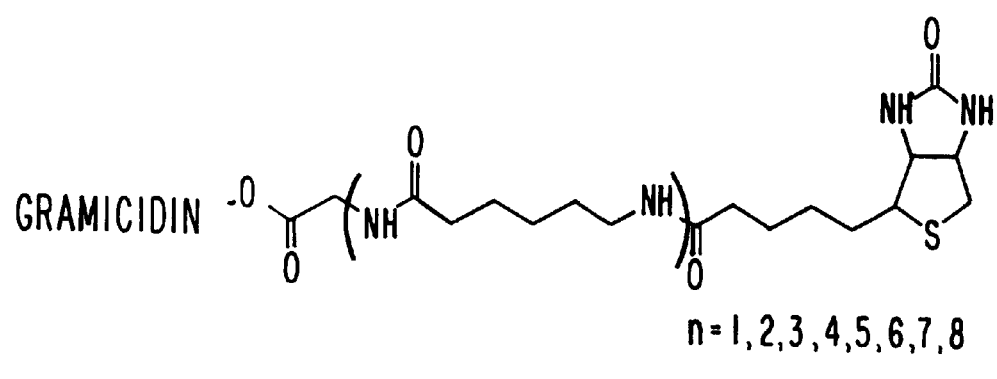
FIG. 11 shows the structure of biotinylated gramicidin E where n=5.

The structure of linker lipid A is shown in FIG. 8; the structure of linker gramicidin B is shown in FIG. 9; the structure of membrane spanning lipid D is shown in FIG. 10; the structure of biotinylated gramicidin E used, where n=5, is shown in FIG. 11.

Thus, a glass slide or plastic suppport is evaporatively coated with a 50 angstrom chromium adhesion layer, followed by a 2000 angstrom layer of gold. The gold coated substrate is placed in an ethanolic solution containing linker lipid A (300 ul of 10 mM solution in ethanol), 2,2'-ethanol disulfide (200 ul of a 10 mM solution in ethanol), linker gramicidin B (100 ul of a 0.01 mg/ml solution in ethanol), membrane spanning lipid D (225 ul of a 1 mM solution in ethanol) and ethanol (50 ml). The gold coated substrate should preferably be placed into this solution within five minutes of preparation. The gold coated substrate is left in this solution for 60 minutes, and then rinsed with ethanol. The gold coated slide is then assembled in an electrode holder such that an electrode is defined, that for the current examples has an area of approximately 16 mm$^2$. Then 5 ul of a solution of 1,2-di(3RS,7R,11R-phytanyl)-sn-glycero-3-phosphocholine and 1,2-di(3RS,7R,11R-phytanyl)glycerol in a 7:3 ratio, 14 mM total lipid concentration in ethanol is added to the surface of the gold electrode and then rinsed with two washes of 500 ul of phosphate buffered saline (PBS), leaving 100 ul PBS above the electrode surface. The amount of PBS left above the electrode is prefeably less than or equal to 100 ul. A counter electrode, typically silver, is immersed in the PBS solution; and the counter electrode and the sensing electrode are connected to an impedance bridge. A DC offset of –300 mV is applied to the sensing electrode during the AC measurement. The electrode assembly is equilibrated to 35° C. This forms the sensing membrane for the case when a probe is used that increases the conductance of the membrane.

EXAMPLE 2

Preparation of Probe Solution

A solution of linker gramicidin B (1 uM and sodium dodecylsulfate (10 UM) in PBS is sonicated in a bath sonicator for 20 minutes. This solution may be stored for at least 12 months at 4° C. Although the gramicidin with sodium dodecylsulfate is stable in aqueous solution, the gramicidin incorporates readily into sensing membranes and produces conducting ion channels. This change in conduction can be monitored using impedance spectroscopy.

EXAMPLE 3

Preparation of an Avidin Coated Solid Support

Polystyrene wells, as used in the preparation of ELISA tests, are treated with a solution of avidin (1 mg/ml) in PBS for 60 minutes, and then rinsed with PBS three times, drained, and then filled with 200 ul of PBS. The polystyrene wells are now coated with avidin.

EXAMPLE 4

Sensing of Small Analyte—ie. biotin

Figure 12:
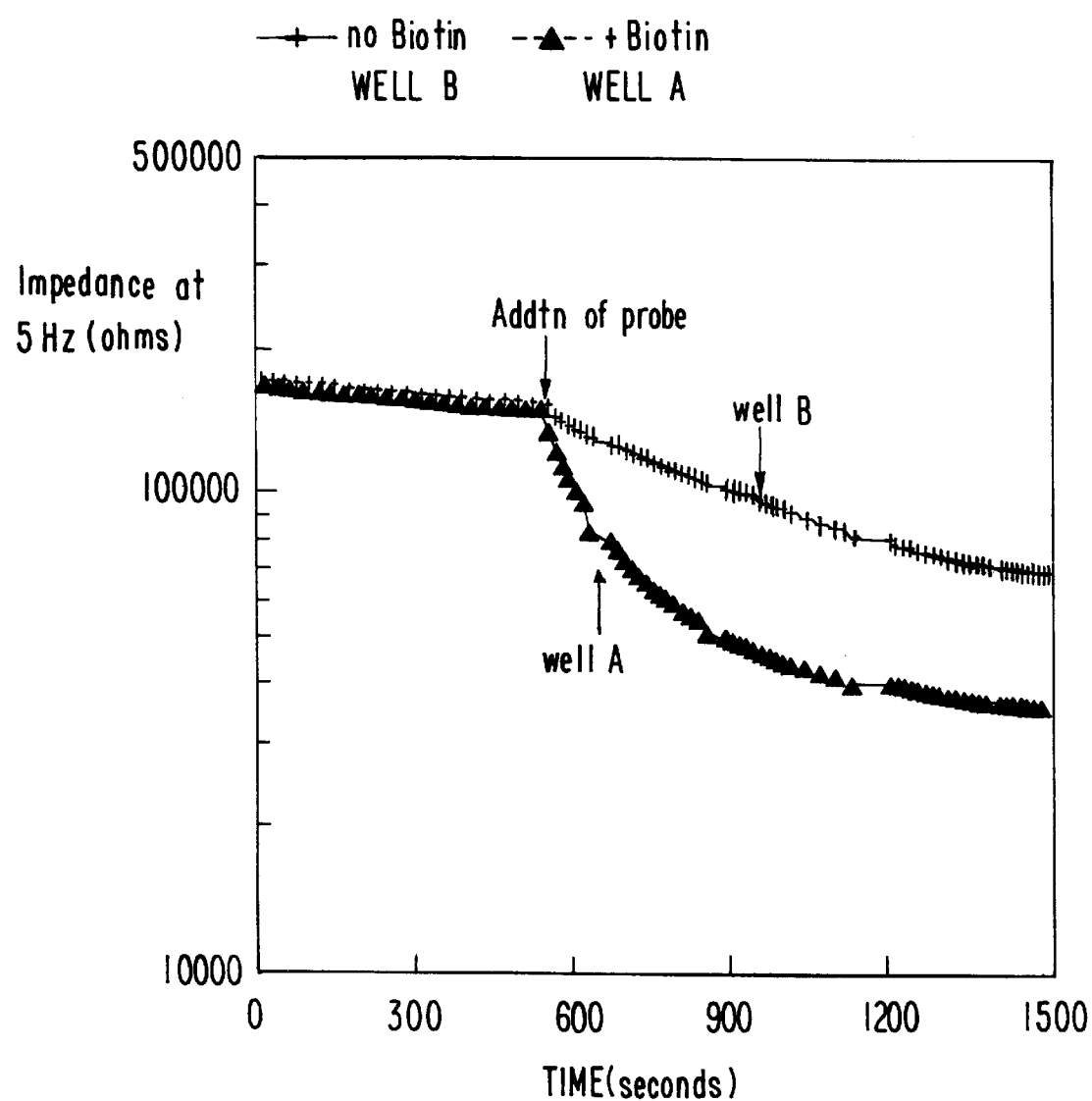
FIG. 12 shows impedance measurements in Example 4.

Two polystyrene wells coated with avidin are prepared as described in example 3—well A and well B. To well A, 5 ul of a test solution containing the analyte biotin (1 mM in PBS) is added and is mixed for 3 minutes. To well B, 5 ul of a test solution containing no biotin is added and mixed for 3 minutes. To both wells A and B, 2.5 ul of the probe solution prepared in example 2 is added and mixed for 5 minutes. It is found that in the presence of the analyte (ie.biotin), the biotin is complexed to the receptor bound to the solid support, in this case avidin, hence preventing the biotinylated gramicidin E from complexing with the avidin on the solid support ie. the biotinylated gramicidin E probe remains in the PBS solution. In the case where no analyte (ie. biotin) is present in solution the receptor sites of the avidin remain uncomplexed and the biotinylated gramicidin E probe is complexed to the solid support ie. the biotinylated gramicidin E is removed from the solution. Next, 100 ul of the solutions from well A and from well B are added to two separate sensing membranes and the conduction of the membrane is monitored using impedance spectroscopy. FIG. 12 shows that the drop in impedance caused by addition of the solution from well A is larger and faster than the drop in impedance caused by addition of solution of well B. Thus the presence or absence of the biotin analyte can be detected. The amount of biotin in the test solution will obviously determine the number of binding sites that the biotin occupies on the receptor on the solid support, which will in turn determine the number of probe molecules left in solution. The rate of change of the impedance properties of the membrane due to the probe will therefore be proportional to the analyte concentration. Alternatively, when the number of probe molecules is limited, the absolute number of probe molecules that affect the membrane may be used to determine the concentration of analyte. It is known in the art that it is possible to measure the conductance of a single gramicidin ion channel in black lipid membranes. It will be appreciated by those skilled in the art that the receptor bound to the solid support may be a receptor such as an antibody specific towards an analyte, and that the gramicidin may have an analogue of the analyte attached such that the gramicidin can bind to the attached receptor via the attached analyte analogue.

EXAMPLE 5

Sensing of Large Analyte—ie. Biotinylated BSA

Figure 13:
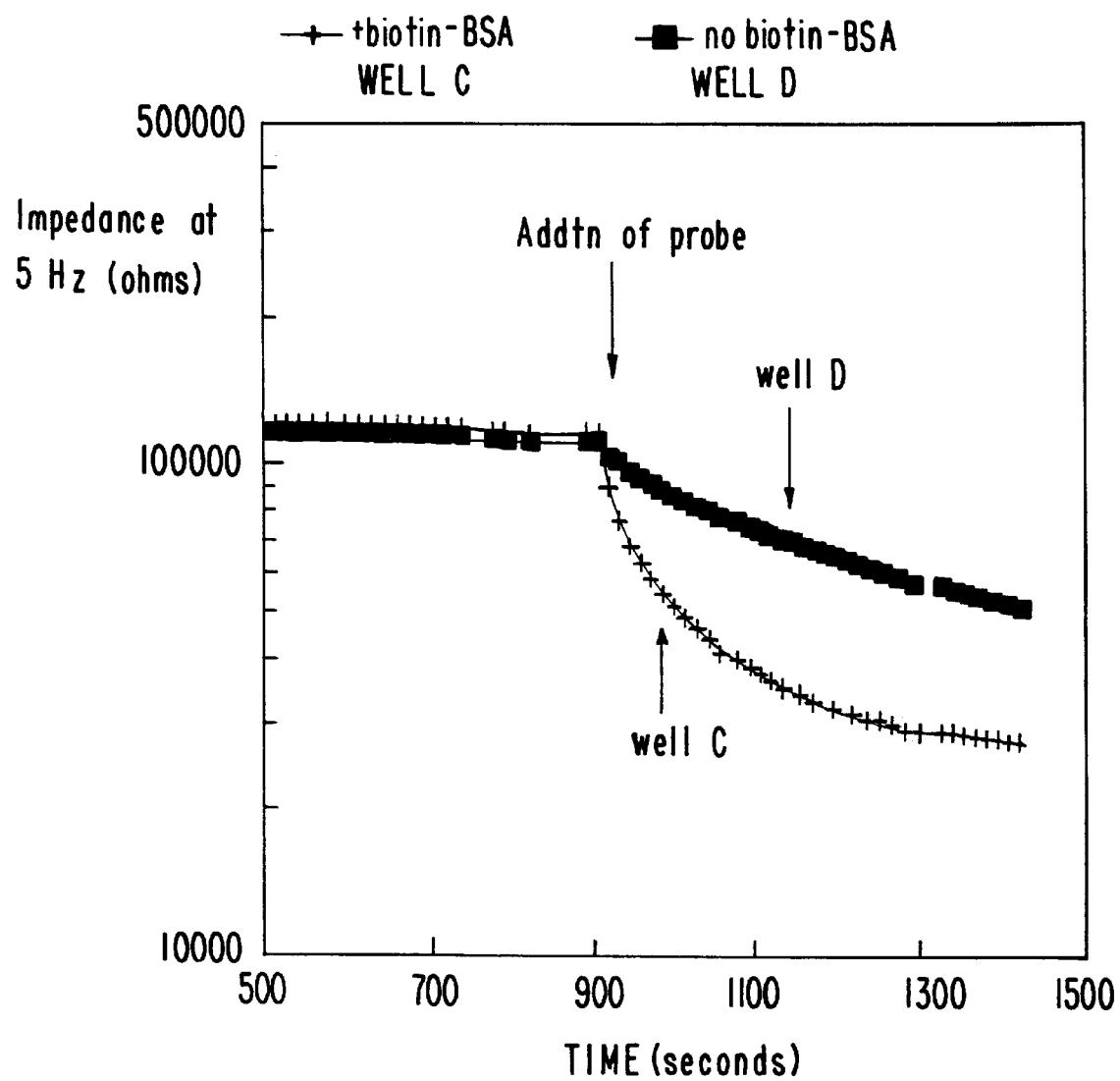
FIG. 13 shows impedance measurements in Example 5.

Two polystyrene wells coated with avidin are prepared as described in example 3—well C and well D. To well C, 5 ul of a test solution containing the analyte biotinylated bovine serum albumin (BSA) (1.3 mg/ml in PBS) is added and is mixed for 10 minutes. To well D, 5 ul of a test solution containing no biotinylated BSA is added and mixed for 10 minutes. To both wells C and D, 2.5 ul of the probe solution prepared in example 2 is added and mixed for 10 minutes. It is expected that in the presence of the analyte ie. biotinylated BSA, the biotinylated BSA is complexed to the receptor bound to the solid support, in this case avidin, hence preventing the biotinylated gramicidin E from complexing with the avidin on the solid support ie. the biotinylated gramicidin E probe remains in the PBS solution. In the case where no analyte (ie. biotinylated BSA) is present in solution the receptor sites of the avidin remain uncomplexed and the biotinylated gramicidin E probe is complexed to the solid support ie. the biotinylated gramicidin E is removed from the solution. Next, 100 ul of the solutions from well C and from well D are added to two separate sensing membranes and the conduction of the membrane is monitored using impedance spectroscopy. FIG. 13 shows that the drop in impedance caused by addition of the solution from well C is larger and faster than the drop in impedance caused by addition of solution of well D. Thus the presence or absence of the biotinylated BSA analyte can be detected.

EXAMPLE 6

Sensing of large analyte—ie. Ferritin

Figure 14:
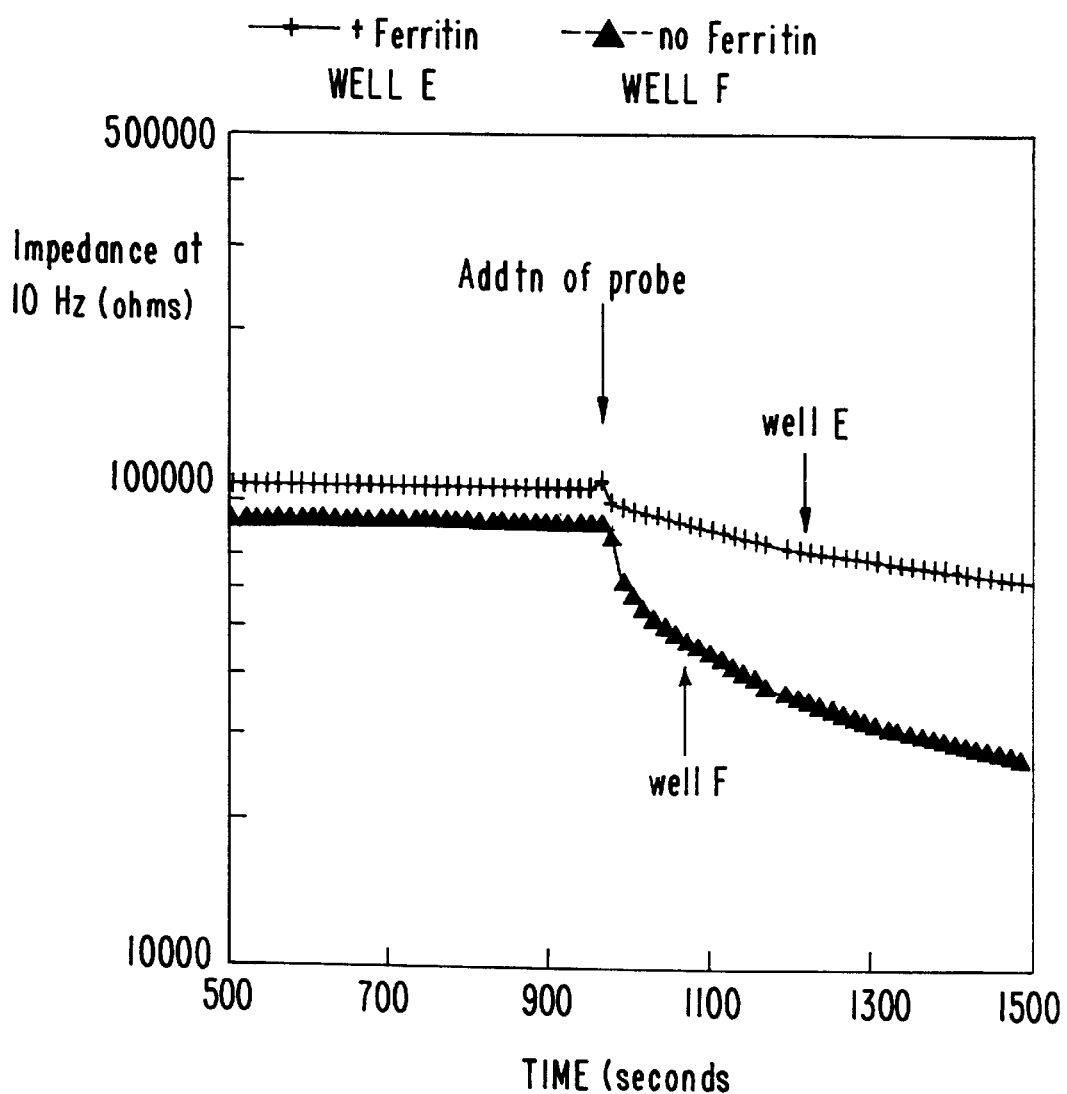
FIG. 14 shows impedance measurements in Example 6.

The polystyrene wells coated with an anti-ferritin antibody from a commercially available ELISA kit for ferritin (Bioclone Australia Pty. Ltd., Marrickville NSW 2204, Elegance Amplified Elisa System, Cat. No. FEA-96) was used. To one well (well E), 200 ul of 500 uM ferritin was added, to another well (well F) 200 ul of PBS without the ferritin analyte was added. Both wells were mixed for six minutes and then washed with three times 400 ul PBS. Then 200 ul of biotinylated anti-ferritin antibody solution from the ELISA kit was added to each well and mixed for 3 minutes. The wells were rinsed with three times 400 ul PBS and 200 ul of 0.025 mg/ml of avidin in PBS was added to both wells and mixed for 5 minutes. The wells were rinsed with three times 400 ul PBS and 200 ul of PBS was left in both wells. To both wells, 2.5 ul of biotinylated gramicidin E/sodium dodecylsulfate probe solution prepared in example 2 was added and mixed for 5 minutes. Next, 100 ul of the solution from well E and from well F were added to two sensing membranes, as prepared in example 1. The change in impedance due to the addition of the probe solution was monitored by impedance spectroscopy. FIG. 14 clearly shows that there is a larger and faster drop in impedance due to the probe solution in the absence of ferritin from the test solution than in the presence of ferritin in the test solution. As will be readily appreciated the rate of change and the amplitude can be used to determine the concentration of the ferritin in an analyte sample.

As will be apparent from the above description the present invention describes devices and methods which run be incorporated into current detection methods for antibody or DNA-based technologies. The invention uses the sensing membranes material described in various patents (e.g. PCT/AU88/00273, PCT/AU89/00352, PCT/AU90/00025, PCT/AU92/00132, PCT/AU93/00590, PCT/AU93/00620 or PCT/AU94/00202) as the detection material. The sensing membrane can be incorporated into single-step devices or used in conventional multi-step processes to replace the enzyme, chemiluminescent, fluorescent, or radiolabelled, probes currently used for the detection of end-product. The type of probes which can be attached to molecules which are used in the final step of antibody or DNA-based technologies include any species which can cause a change in conduction through the membrane.

For example, probes such as ion channels can insert themselves into the membrane and allow ion flow across an insulting membrane. Other probes can cause leaking paths across insulating membranes by specifically binding to sites on the membrane and inducing either phase separation or aggregation of molecules, solubilising the membrane, or removing a section of the membrane.

Other probes may reduce the ion flow across the channel by interacting with ion channels already present in the membrane. For example, using streptavidin or avidin as the probe for interaction with membranes containing biotinylated gramicidin will reduce ion flow across the membrane.

The effect on the membrane can be amplified by the use of multiprobes, such as latex or polystyrene beads with a large number of streptavidins bound to them to reduce ion flow, or abound to ion channels to include ion flow across the membrane.

The advantages of the sensing membrane as detection mechanism in antibody or DNA-based technologies is the speed and simplicity of the readings. Ion flow changes can be measured by impedance changes at a variety of frequencies or at a single frequency. Single-channel measurements of, for example, gramnicidin, are routinely carried out using black lipid membranes, and offer the potential for extremely sensitive measurements. Impedance measurements require simple computational equipment which can also be reduced in size to portable dimensions. Reagents are simplified and do not rely on colour changes or light-emitting species for detection.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An analyte detection device comprising:
a membrane including ligands reactive with an analyte;
means to measure the impedance of the membrane; and
means to move an analyte bound to the ligands away from the membrane without disrupting the binding of the ligands to the analyte; wherein the movement of the analyte away from the membrane causes a change in the impedance of the membrane, in which the membrane ligands are attached to amphiphiles of the membrane, movement of the analyte causing extraction of the ligands and attached amphiphiles from the membrane.

2. An analyte detection device comprising:
a membrane including ligands reactive with an analyte;
means to measure the impedance of the membrane; and
means to move an analyte bound to the ligands away from the membrane without disrupting the binding of the ligands to the analyte; wherein the movement of the analyte away from the membrane causes a change in the impedance of the membrane, in which the membrane ligands are attached to ionophores within the membrane, movement of the analyte causing extraction of the ligands and attached ionophores from the membrane.

3. An analyte detection device as claimed in claim 2 in which the ionophores are gramicidin.

4. An analyte detection device comprising:
a membrane including ligands reactive with an analyte;
means to measure the impedance of the membrane; and
means to move an analyte bound to the ligands away from the membrane without disrupting the binding of the ligands to the analyte; wherein the movement of the analyte away from the membrane causes a change in the impedance of the membrane, in which the analyte is bound to a carrier via a plurality of second ligands.

5. An analyte detection device as claimed in claim 4 in which the carrier is a bead, or a charged or magnetic particle.

6. An analyte detection device as claimed in claim 4 in which the means to move the analyte comprises an electric field.

7. An analyte detection device comprising first and second zones, means to allow addition of a probe to the first zone, means to allow addition of a sample suspected to contain an analyte and means to allow passage of the probe from the first zone the second zone; the first zone containing ligands reactive with the analyte and the second zone including a membrane the level of impedance of which is dependent on the presence or absence of the probe and means to measure the impedance of the membrane, and in which the membrane comprises a first and second layer of a closely packed array of amphiphilic molecules and a plurality of ionophores comprising a first and second half membrane spanning monomers, the first half membrane spanning monomers being provided in the first layer and the second half membrane spanning monomers being provided in the second layer, the second half membrane spanning monomers being capable of lateral diffusion within the second layer independent of the first half membrane spanning monomers, the first half membrane spanning monomers being prevented from lateral diffusion in the first layer, and a second ligand provided on at least the second half membrane spanning monomers, said second ligand binding to the probe or a portion thereof, the binding of the probe to the second ligand causing a change in the relationship between the first half membrane spanning monomers and the second half membrane spanning monomers such that the flow of ions across the membrane via the ionophores is allowed or prevented, and measuring the impedance of the membrane.

8. An analyte detection device as claimed in claim 7 in which the probe includes an ionophore.

9. The device as claimed in claim 8 in which the ionophore is gramicidin.

10. An analyte detection device as claimed in claim 7 in which the ligands in the first zone are antibodies or binding fragments thereof.

11. An analyte detection device as claimed in claim 7 in which a proportion of the amphiphilic molecules are membrane spanning amphiphiles, the membrane spanning amphiphiles being archeobacterial lipids or tail to tail chemically linked bilayer amphiphiles.

12. An analyte detection device as claimed in any one of claims 7 or 11 in which the half membrane spanning monomers are gramicidin monomers.

13. An analyte detection device as claimed in any one of claims 7, 11, or 12 in which the membrane includes a plurality of third ligands reactive with the probe or a portion thereof attached to amphiphiles in the membrane.

14. An analyte detection device as claimed in claim 13 in which the amphiphiles are membrane spanning amphiphiles.

15. An analyte detection device as claimed in claim 13 or claim 14 in which the third ligands are prevented from diffusing laterally within the membrane.

16. An analyte detection device as claimed in any one of claims 7, 11–15 in which the membrane is attached to an electrode such that a reservoir exists between the electrode and the membrane.

* * * * *